(12) United States Patent
Gottlieb et al.

(10) Patent No.: US 7,500,949 B2
(45) Date of Patent: Mar. 10, 2009

(54) MULTILUMEN CATHETER

(75) Inventors: Rebecca Gottlieb, Culver City, CA (US); Rajiv Shah, Rancho Palos Verdes, CA (US); Mary M. Morris, Mounds View, MN (US); Victor Giron, North Hills, CA (US); Michael E. Miller, Los Angeles, CA (US); Bradley J. Enegren, Moorpark, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 711 days.

(21) Appl. No.: 10/331,949

(22) Filed: Dec. 30, 2002

(65) Prior Publication Data
US 2004/0064086 A1     Apr. 1, 2004

Related U.S. Application Data

(60) Provisional application No. 60/414,248, filed on Sep. 27, 2002, provisional application No. 60/360,940, filed on Mar. 1, 2002.

(51) Int. Cl.
  *A61B 5/00* (2006.01)
  *A61B 5/05* (2006.01)
  *A61M 5/00* (2006.01)
  *A61M 35/00* (2006.01)
(52) U.S. Cl. .................. 600/300; 600/309; 600/347; 600/365; 604/264
(58) Field of Classification Search ............. 604/544; 600/347, 365, 435, 466, 526
See application file for complete search history.

(56) References Cited

U.S. PATENT DOCUMENTS 4,340,615 A    7/1982    Goodwin et al.

(Continued)

FOREIGN PATENT DOCUMENTS

EP    0 711 574 A1    5/1996
EP    1 145 731 A2    10/2001

OTHER PUBLICATIONS

PCT International Search Report as issued in International Application Number PCT/US03/06097, Mailing date Mar. 15, 2004.
European Search Report for EP Application 03711295.0 -2310 dated Dec. 28, 2006.
European Search Report for EP Application 03711295.0 -2310 dated Sep. 11, 2006.

*Primary Examiner*—Patricia C Mallari
(74) *Attorney, Agent, or Firm*—Foley & Lardner LLP

(57) ABSTRACT

A multilumen catheter having tubings extending into lumens within the catheter. The lumens may be used for blood, drugs or other medicants. The lumens may also be used for sensors. The junction element, external to the patient, connects the tubings to the lumens. The tubings, also external to the patient, connect to infusion members, to which one or more infusion systems may be connected to deliver blood, drugs and other medicants to the patient. A sensor having a sensing element may extend through the sensor lumen and be positioned internal to the patient for physiological parameter sensing. An external portion of the sensor may be connected to associated electronics to provide automatic monitoring of the physiological parameters and automatic delivery and control of the infusants. Also, a central line catheter for delivering fluids directly into a main artery or vein near the heart, which contains a first lumen to deliver a fluid through the central line catheter and a second lumen containing a sensor capable indicating a characteristic level in blood. The first lumen delivers the fluid downstream of the sensor to prevent any interference between the fluid delivery and the sensor readings. In other versions, the central line catheter can have additional lumens for additional purposes. In addition, the central line catheter can further include a flush sleeve to remove debris around the sensor.

27 Claims, 14 Drawing Sheets

U.S. PATENT DOCUMENTS

| | | | |
|---|---|---|---|
| 4,403,984 A * | 9/1983 | Ash et al. | 604/503 |
| 4,601,697 A | 7/1986 | Mammolenti et al. | |
| 4,674,518 A * | 6/1987 | Salo | 600/508 |
| 4,721,115 A * | 1/1988 | Owens | 600/526 |
| 5,000,190 A | 3/1991 | Petre | |
| 5,108,369 A * | 4/1992 | Ganguly et al. | 604/102.02 |
| 5,250,038 A * | 10/1993 | Melker et al. | 604/264 |
| 5,272,012 A * | 12/1993 | Opolski | 428/423.1 |
| 5,423,744 A | 6/1995 | Gencheff et al. | |
| 5,531,679 A * | 7/1996 | Schulman et al. | 604/65 |
| 5,700,253 A * | 12/1997 | Parker | 604/526 |
| 5,722,415 A * | 3/1998 | Rom et al. | 600/508 |
| 5,797,869 A * | 8/1998 | Martin et al. | 604/43 |
| 5,928,155 A * | 7/1999 | Eggers et al. | 600/526 |
| 5,976,103 A | 11/1999 | Martin | |
| 6,299,583 B1 | 10/2001 | Eggers et al. | |
| 2003/0125613 A1* | 7/2003 | Enegren et al. | 600/347 |

* cited by examiner

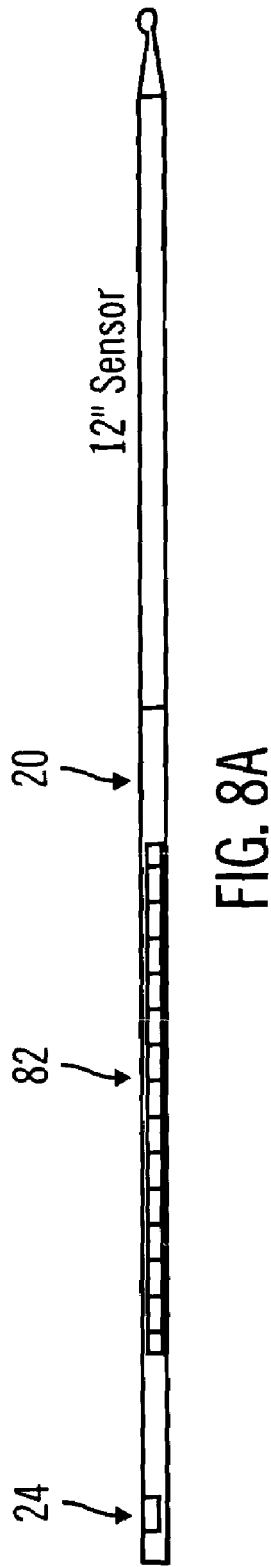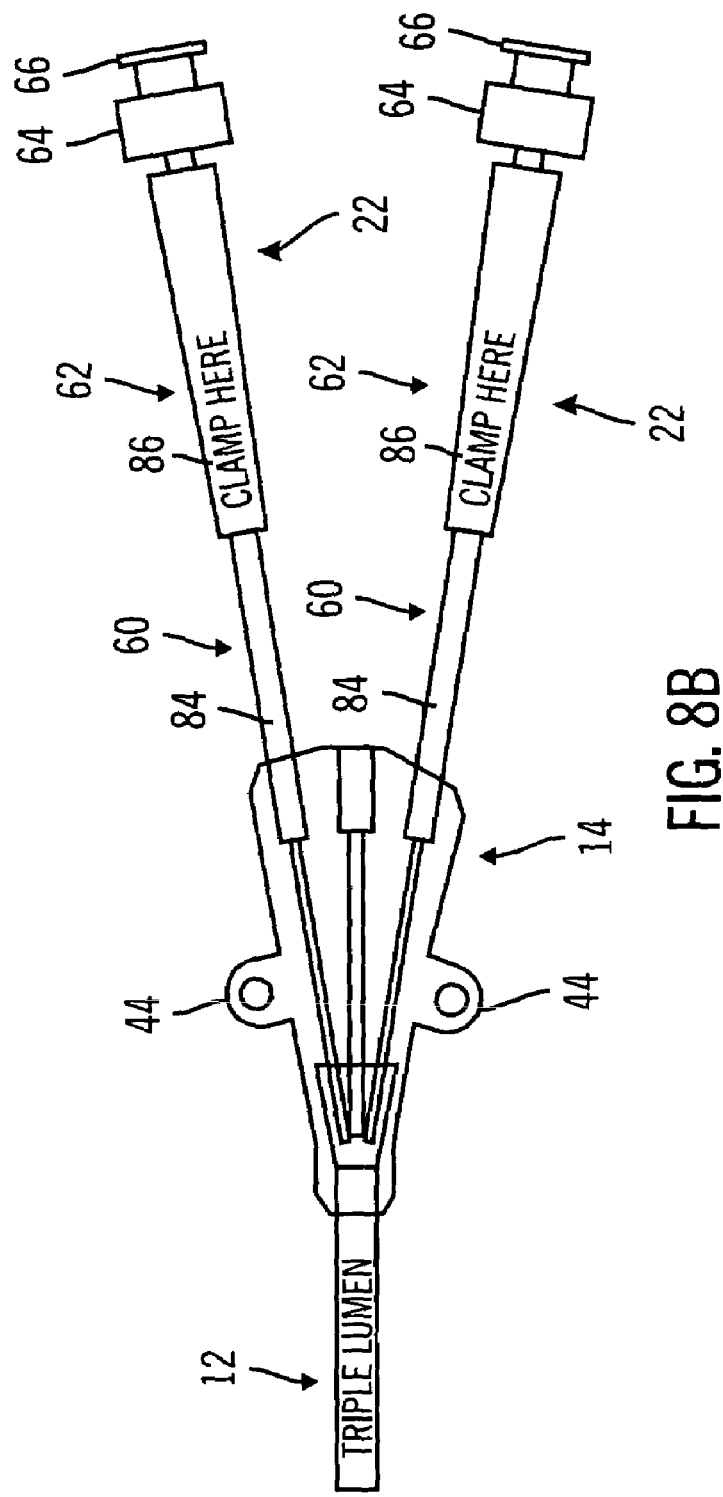
FIG. 8A
FIG. 8B

MULTILUMEN CATHETER

CROSS-REFERENCE TO RELATED APPLICATIONS

Embodiments of the present invention relate to U.S. Provisional Application Ser. No. 60/414,248, filed Sep. 27, 2002, entitled "Multilumen Catheter," which is incorporated by reference herein and is a basis for a claim of priority, and to U.S. Provisional Application Ser. No. 60/360,940, filed Mar. 1, 2002, entitled "System and Method of Monitoring Analyte Concentrations Through a Central Line," which is also incorporated by reference herein.

BACKGROUND

1. Field of the Invention

This invention relates to the field of catheters and analyte and therapy sensors used in biomedical applications and, in particular, to a catheter having multiple lumens and a process of making and using the same and to analyte and therapy sensors used in critical care situations.

2. Description of Related Art

The accurate and timely monitoring of vital signs and other biomedical or physiological parameters in a critical care or intensive care setting can often mean the difference between success and disaster for patients and the medical care providers rendering treatment for those patients. For such patients, the quality of life and, possibly, even life itself may depend on such monitoring.

Some types of physiological parameter monitoring, while critical, have traditionally been slow and cumbersome. For example, for patients who are in an intensive care environment, especially those with diabetes, glucose monitoring is critical. If the amount of glucose in a patient's system is not maintained at proper levels, the patient may sustain serious or life-threatening injury. If too much glucose accumulates in the patient's system, the patient could become hyperglycemic, resulting in shortness of breath, nausea and vomiting at best or coma and death in the worst case. If there is too little glucose in the patient's system, the patient could become hypoglycemic, resulting in dizziness, sweating and headache at best and unconsciousness and death in the worst case.

Glucose monitoring in a critical care or intensive care environment has typically been done manually. For example, in some facilities, if a patient with diabetes is in a critical or intensive care environment, a medical care provider draws a sample of blood from the patient and sends it to a lab, hopefully on site, for glucose analysis. Based on the results of the analysis, the patient is treated accordingly, possibly with insulin or glucose infusion depending on whether the patient is hyperglycemic or hypoglycemic, respectively. This process, i.e., drawing a sample of blood from the patient, transferring the blood to a laboratory for analysis, transferring the results of the analysis back to the patient's medical care provider, reviewing the analysis, recommending a suitable treatment, and administering the treatment, can be cumbersome and is prone to human error.

Ideally, and for the benefit of the patient, the time between admission of the patient to the critical or intensive care ward to the time of drug infusion and stabilization of blood glucose levels is minimal. However, given the nature of laboratory diagnostics and manual analysis, the time lag from patient admission to glucose analysis and, ultimately, to treatment is sometimes longer than desirable.

In addition, for treatment to be rendered to the patient, one or more catheters may be inserted into the patient's body. For example, if treatment of the patient necessitates infusions of blood and insulin, blood and drugs, blood and glucose or the like, traditional caregivers have placed two separate catheters into the patient's body and connected each catheter to an appropriate infusion delivery system. For each catheter used, a separate catheter tunneling procedure must be performed, which can be very uncomfortable for the patient physically. Moreover, for each catheter exiting the patient's body, the risk that a catheter is disturbed, accidentally displaced or otherwise interfered with increases. Also, multiple catheters can increase the risk of infection.

Over the years, bodily characteristics have been determined by obtaining a sample of bodily fluid. For example, diabetics often test for blood glucose levels with a blood glucose meter. Traditional blood glucose determinations have utilized a painful finger prick using a lancet to withdraw a small blood sample that is used by the blood glucose meter. However, in critical care situations, these discrete blood meter readings are inefficient in closely monitoring blood characteristics since they would need to be taken every minute to provide near continuous data required during critical care situations.

Long-term implanted sensors have been proposed that can stay in the body for long periods of time, such as weeks and months. These long-term implanted sensors are particularly well adapted in delivering dependable data over a period of time as well as detecting immediate changes in blood characteristics since they are implanted in one of the main arteries near the heart. However, these sensors need to be implanted in a separate procedure, often not feasible for critical care patients. Moreover, although an implanted sensor (e.g. a glucose sensor) may make sense for diabetic patients needing long term care of the disease, non-diabetic patients may not need a long-term implanted sensor outside the intensive care unit.

SUMMARY

Accordingly, there is a need for a catheter having multiple lumens that can deliver one or more infusants to a patient. There is also a need for a catheter having one or more lumens for a sensing element that can be located at an appropriate position in the body of a patient to monitor vital signs and other biomedical parameters. There is also a need for a catheter that can provide signals for automatic analysis of vital physiological parameters for monitoring the control and delivery of infusants to a patient.

Embodiments of the present invention relate to a catheter having one lumen or multiple lumens that can deliver one or more infusants to a patient. Embodiments of the present invention include a catheter having one or more lumens for a sensing element that can be located at an appropriate position in the body of a patient to monitor vital signs and other biomedical parameters. Embodiments of the present invention include a catheter that can provide signals for automatic analysis of vital physiological parameters for monitoring the control and delivery of infusants to a patient. Embodiments of the present invention also relate to an improved method and system for detecting a blood characteristic of a patient in an intensive care unit, which obviates for practical purposes, the above-mentioned limitations.

A multilumen catheter according to an embodiment of the present invention includes a first tubing, at least one lumen disposed within the first tubing, a junction element and at least one second tubing. The multilumen catheter may further include an insertion piece that attaches to the at least one second tubing. The at least one lumen may be extruded from the first tubing.

The first tubing may be coated with a lubricious coating such as, for example, siloxane. The at least one second tubing may include a first infusant tubing, a second infusant tubing and a sensor tubing. Likewise, the at least one lumen may include a first infusant lumen, a second infusant lumen and a sensor lumen. The first infusant tubing may extend into the first infusant lumen, the second infusant tubing may extend into the second infusant lumen and the sensor tubing may extend into the sensor lumen. Also, the at least one second tubing may extend into the at least one lumen.

According to an embodiment of the present invention, the first infusant lumen and the second infusant lumen exit the first tubing at the same location. According to another embodiment of the present invention, the first infusant lumen and the second infusant lumen exit the first tubing at different locations. Also, a sensor lead, which may have a sensing element, may extend through the sensor tubing and the sensor lumen. The sensing element may be positioned distal to the first tubing or may be positioned proximal to the first tubing.

According to an embodiment of the present invention, infusion members may be connected to the first and second tubings. The infusion members may include fittings, such as, for example, injection sites, caps and clamps.

A method for using a multilumen catheter according to an embodiment of the present invention may include inserting a distal end of the multilumen catheter into a patient, affixing an external, proximal end of the multilumen catheter to the patient, and affixing infusion members to the external, proximal end of the multilumen catheter. The method may also include affixing electronic elements to the external, proximal end of the multilumen catheter.

According to an embodiment of the present invention, a multilumen catheter may include, a first lumen having a contour and a plurality of second lumens having contours complementary to the first lumen, wherein the contour of the first lumen and the contours of the plurality of second lumens maximize an inner volume of the first lumen and an inner volume of the plurality of the second lumens and minimize an outer dimension of the first lumen and an outer dimension of the plurality of the second lumens. One of the plurality of second lumens may be shaped to provide a path for a guide wire. The first lumen may be used for a sensor lead and at least one of the plurality of second lumens is used for drug delivery and/or blood product infusion.

The multilumen catheter may also include a first tubing connected to the first lumen, a plurality of second tubings connected to the plurality of second lumens, infusion sources connected to the plurality of second tubings, and a containment element surrounding the first tubing and the plurality of second tubings for maintaining the position of the first tubing and the plurality of second tubings.

According to an embodiment of the invention, a central line catheter for delivering fluids directly into a main artery or vein near the heart contains a first lumen to deliver a fluid through the central line catheter and a second lumen containing a sensor capable of indicating a characteristic level in blood, wherein the first lumen delivers the fluid downstream of the sensor to prevent any interference between the fluid delivery and the sensor readings. The first lumen may also deliver fluid upstream of the sensor. In addition, the central line catheter can have additional lumens for additional purposes. In particular embodiments, the central line catheter further includes a flush sleeve to remove debris, such as, for example, biological debris, around the sensor. In still other embodiments, the sensor is an analyte or therapy sensor, such as, for example, a glucose analyte sensor.

According to another embodiment of the invention, a system for delivering and monitoring a condition in an intensive care unit is provided. The system contains a central line catheter comprising a first lumen to deliver fluid and a second lumen containing a sensor capable of indicating a characteristic level in blood; an infusion device for delivering fluid through the first lumen; and a monitoring device for displaying readings obtained by the sensor.

Other features and advantages of the invention will become apparent from the following detailed description, taken in conjunction with the accompanying drawings, which illustrate, by way of example, various features of embodiments of the invention.

BRIEF DESCRIPTION OF THE DRAWINGS

FIG. 8a shows a plan view of markings on a sensor lead according to an embodiment of the present invention.

FIG. 8b shows a plan view of markings on infusion members according to an embodiment of the present invention

DETAILED DESCRIPTION

In the following description of preferred embodiments, reference is made to the accompanying drawings which form a part hereof, and in which are shown by way of illustration specific embodiments in which the invention may be practiced. It is to be understood that other embodiments may be utilized and structural changes may be made without departing from the scope of the present invention.

Figure 1:
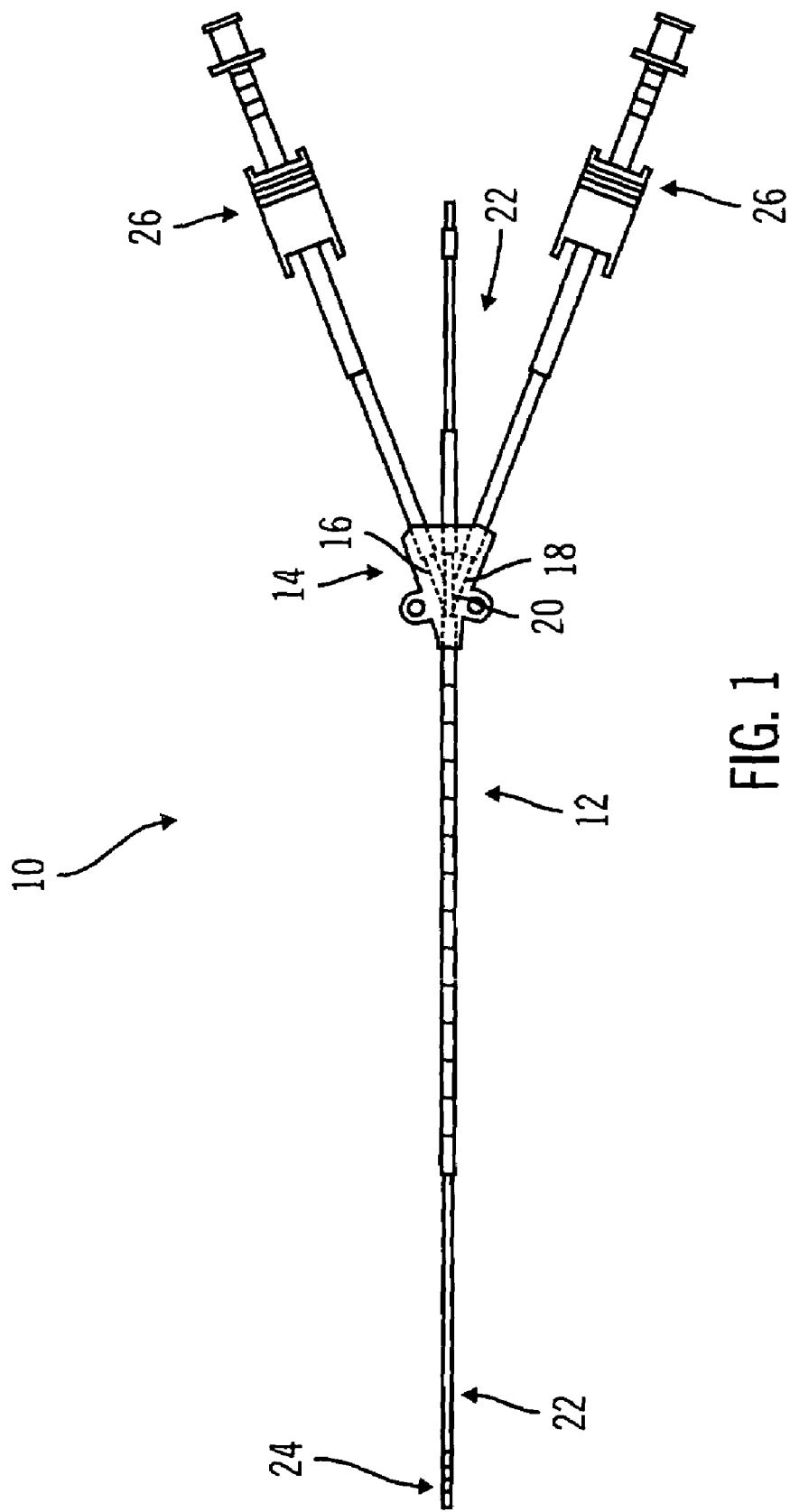
FIG. 1 shows a plan view of a generalized multilumen catheter according to an embodiment of the present invention.

A generalized multilumen catheter 10 according to an embodiment of the present invention is shown in FIG. 1. The multilumen catheter 10 includes, without limitation, a lumen tubing 12 having lumens within its interior, a junction element 14, a first infusion tubing 16 connected to one of the lumens within the interior of the lumen tubing 12, a second infusion tubing 18 connected to one of the lumens within the interior of the lumen tubing 12, a sensor tubing 20 connected to one of the lumens within the interior of the lumen tubing 12, a sensor lead 22 and infusion members 26. A distal end of the sensor lead 22 also includes a sensing element 24.

In one example embodiment, the lumen tubing 12 may be inserted into a patient percutaneously such that the sensing element 24 is located at a desired in vivo location. A sensing element suitable for this type of embodiment is disclosed in a patent application entitled "Sensing Apparatus and Process," Ser. No. 10/036,093, filed Dec. 28, 2001, which is hereby incorporated by reference, and in a patent application entitled "Sensor Substrate and Method of Fabricating Same," Ser. No. 10/038,276, filed Dec. 31, 2001, which is also hereby incorporated by reference. In another example embodiment, the multilumen catheter 10 may be fully implanted into the body of a patient.

The junction element 14, the first infusion tubing 16, the second infusion tubing 18, the sensor tubing 20 and the infusion members 26 are located external to the patient. Thus, the infusion members 26 may be connected to infusion delivery systems such that blood products, medicines and other infusants may be delivered to the patient through the various tubings. The external portion of the sensor lead 22 may be connected to data acquisition equipment, monitoring equipment, or other electronic devices to provide feedback, to control the delivery of infusants, to provide other control functions and the like.

The overall length of the multilumen catheter 10 may vary according to the size of the patient. For example, according to an embodiment of the present invention, the overall length of the lumen tubing 12 may be any suitable length from about 9 to 14 inches measured from a point on the first infusion tubing 16 or the second infusion tubing 18 where infusants enter the tubings to the distal end of the lumen tubing 12 where the first infusion tubing 16, the second infusion tubing 18 and the sensor tubing 20 terminate. The sensor lead 22, according to an embodiment of the present invention, may be any suitable length from about 12 to 16 inches in length. The sensor lead 22 may be positioned such that the sensing element 24 is located distal to the end of the lumen tubing 12. According to another embodiment of the present invention, the sensor lead 22 may be positioned such that the sensing element 24 is located at the end of the lumen tubing 12.

Also, according to one embodiment of the present invention, the outer diameter of the lumen tubing 12 is less than 0.120 inches. Maintaining the outer diameter of the lumen tubing 12 at less than 0.120 inches may facilitate insertion of the lumen tubing 12 into a patient. According to another embodiment of the present invention, the outer diameter of the lumen tubing 12 is less than 0.140 inches. According to yet another embodiment of the present invention, the outer diameter of the lumen tubing 12 is about 0.130 inches.

Figure 2:
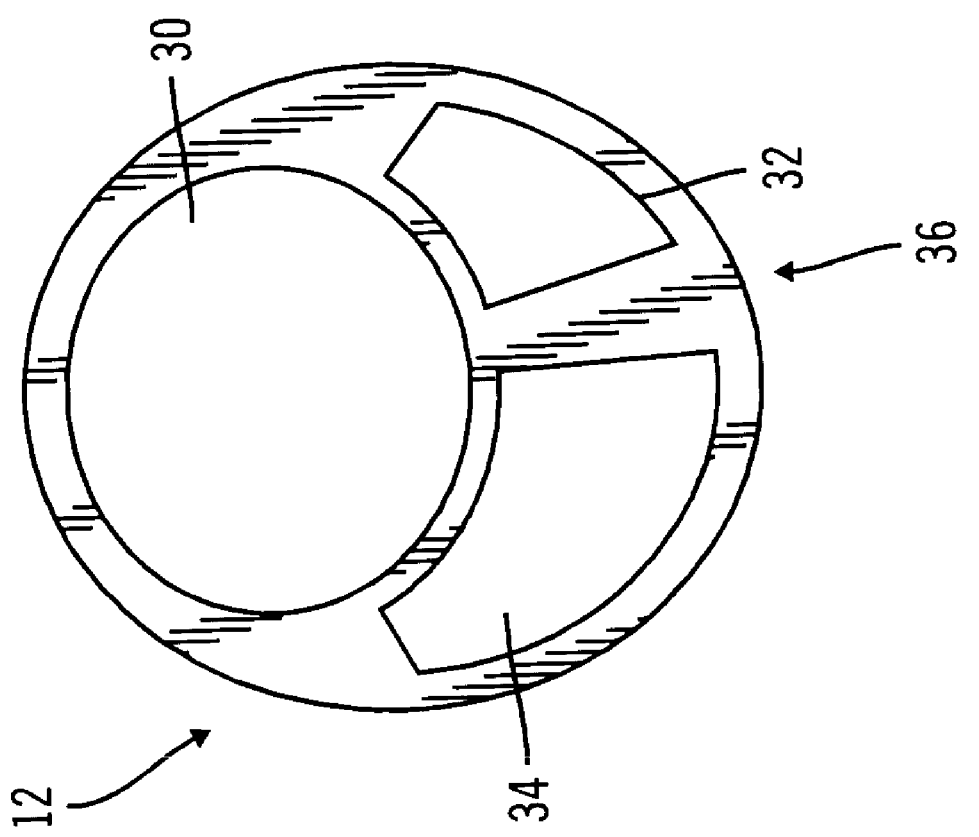
FIG. 2 shows an internal portion of a lumen tubing according to an embodiment of the present invention.

An internal portion of the lumen tubing 12 according to an embodiment of the present invention is shown in FIG. 2. In FIG. 2, three lumens, a sensor lumen 30, a drug lumen 32 and a blood lumen 34 are formed within the interior of the lumen tubing 12. As can be seen, the lumens form isolated paths within the lumen tubing 12.

The lumens may be formed within the interior of the lumen tubing 12 by a variety of methods. For example, in the embodiment shown, the sensor lumen 30, the drug lumen 32 and the blood lumen 34 have been extruded out of silicone. However, any method of lumen tubing formation that is suitable in the industry may be used depending on the application and environment for the catheter, including, but not limited to, extrusion, molding, machining or combinations thereof. In addition, materials other than silicone may be used for the catheter, including, but not limited to, polyurethane, polyethylene, Teflon, PVC, Elastomeric, hydrogel and the like.

For example, if a Swan-Ganz catheter, which typically has five lumens, all with a special purpose, were adapted for use with embodiments of the present invention, it could be modified by adding an additional lumen to provide a location for a sensor. Thus, a Swan-Ganz catheter could be fabricated with six lumens to accommodate a sensor. Also, the size of the sensor may be modified to accommodate the size of the lumen.

Embodiments of the present invention may also be adapted for use with Peripherally Inserted Central Catheter (PICC) lines. A PICC line could be fabricated similar to a central line catheter, but, according to embodiments of the present invention, could be smaller and longer.

Embodiments of the present invention may also be adapted for use with double lumen central line catheters. For example, in adapting embodiments of the present invention to a double lumen central line catheter, the catheter may include one lumen for an infusant and one lumen for a sensor.

The lumens formed within the interior of the lumen tubing 12 may be formed into a variety of sizes and shapes. For example, as can be seen in FIG. 2, the sensor lumen 30 has been extruded such that its horizontal dimension is slightly longer than its vertical dimension, i.e., it is somewhat oval in shape. The sensor lumen 30, according to this embodiment, has been formed in this way due to the nature of the sensor lead 22 that will be placed into it.

For example, because there may be loose pieces in the sensor lead 22, the sensor lumen 30 may be formed such that it provides a compression fit for the sensor lead 22. Thus, the oval shape of the sensor lumen 30 was chosen for this particular embodiment. An oval shape facilitates compression as follows: in the horizontal direction, the lumen is the same size as the horizontal direction of the sensor (there are no "loose parts" in this direction); in the vertical direction (the direction on the sensor which has assembled loose parts), the lumen is undersized so that the sensor is "squeezed" into placed. However, other shapes may be chosen for the sensor lumen 30 or any of the other lumens that may exist within the interior of the lumen tubing 12 depending on the application.

The drug lumen 32 and the blood lumen 34 have also been shaped to facilitate the nature of their uses. For example, because both the drug lumen 32 and the blood lumen 34 reside alongside the sensor lumen 30, which has been formed in a quasi-oval shape, a portion of one side of each of the drug lumen 32 and the blood lumen 34 has been formed to also be somewhat oval in shape such that the curved portions of the drug lumen 32 and the blood lumen 34 follow the contour of the sensor lumen 30. This allows for maximizing lumen cross-section area (or volume), while minimizing overall outer diameter of the catheter. The blood lumen 34 may be configured to maximize volume within the dimensions of the lumen tubing because, for some applications, it is necessary that the blood lumen 34 be directed around a guide wire. Because of the flexible nature of the catheter, it is sometimes difficult to maneuver the catheter through the body of a patient. In practice, it is sometimes desirable to first insert a rigid guide wire into the patient and then maneuver the catheter into the patient by directing it about the guide wire such that the guide wire is eventually positioned inside a lumen. Once the catheter is in the desired location, the guide wire may be removed, leaving the catheter in the proper position.

In addition, the blood lumen 34, according to the embodiment shown in FIG. 2, is configured with minimal sharp corners, or "stagnant zones," as possible. A "stagnant zone" is a portion of the lumen where blood may clot. Because blood clotting is generally an undesirable effect, the blood lumen 34 has been configured to minimize sharp corners so as to prevent blood clotting.

The physical locations of the lumens within the interior of the lumen tubing 12 depend on a variety of factors. For example, as was mentioned above, in the embodiment shown in FIG. 2, the location of the drug lumen 32 and the blood lumen 34 is dictated, in part, due to the location and shape of the sensor lumen 30. In addition, in the embodiment shown in FIG. 2, the drug lumen 32 and the blood lumen 34 has been positioned such that a strut 36 is formed between them. The strut 36 may provide additional strength for the sensor lumen 30, which may be advantageous if, for example, the distal end of the sensor lead 22 (where the sensing element 24 is located) does not extend past the end of the lumen tubing 12. Generally, the lumens that are formed within the lumen tubing 12 may be formed such that they generate structural elements within the interior of the lumen tubing 12 from the material used for the interior of the lumen tubing 12.

Also, the drug lumen 32 and the blood lumen 34 may be formed such that they exit the lumen tubing 12 at the same site, for example, to facilitate manufacturing of the multilumen catheter. However, the drug lumen 32 and the blood lumen 34 need not exit at the same site and, instead, may exit at different sites depending on the application of the multilumen catheter. Although sensor reading interference may be prevented by having a "downstream" exit site, it is possible to have an "upstream" exit site without any corruption of sensor information. For example, if a Swan-Ganz catheter is adapted to embodiments of the present invention, the Swan-Ganz catheter may be used to measure cardiac output using a cold-fluid dilution technique in which a bolus of a cold solution is infused at a known temperature. The temperature may then be measured at a known point downstream. The temperature difference is based on the volume of fluid passing from the initial infusion point to the temperature measurement point based on time.

Lumens may be formed to exit at different sites in a variety of ways. For example, staggered exit sites may be formed by: 1) forming a back-filled tip of one lumen with stamped side ports; 2) terminating one lumen "early" by trimming the tubing or molding a shortened lumen; or 3) forming an adhered "nose cone" that directs fluid (either through a side exit site, or a shortened lumen).

The sensor lead 22 and the sensing element 24 may also be placed in a variety of locations in relation to the lumen tubing 12. For example, the sensor lead 22 may be placed proximal to the lumen tubing 12 such that the sensing element 24 rests at one end of the lumen tubing 12. If this location is chosen for the sensing element 24, according to one embodiment of the present invention, it may be advantageous to provide tubing at the end of the lumen tubing 12 that is radio opaque to x-rays so that the position of the catheter tip may be identified under x-ray. If the sensing element 24 is positioned distal to the lumen tubing 12, it will itself be visible under x-ray and its position may easily be determined under x-ray.

Figure 3:
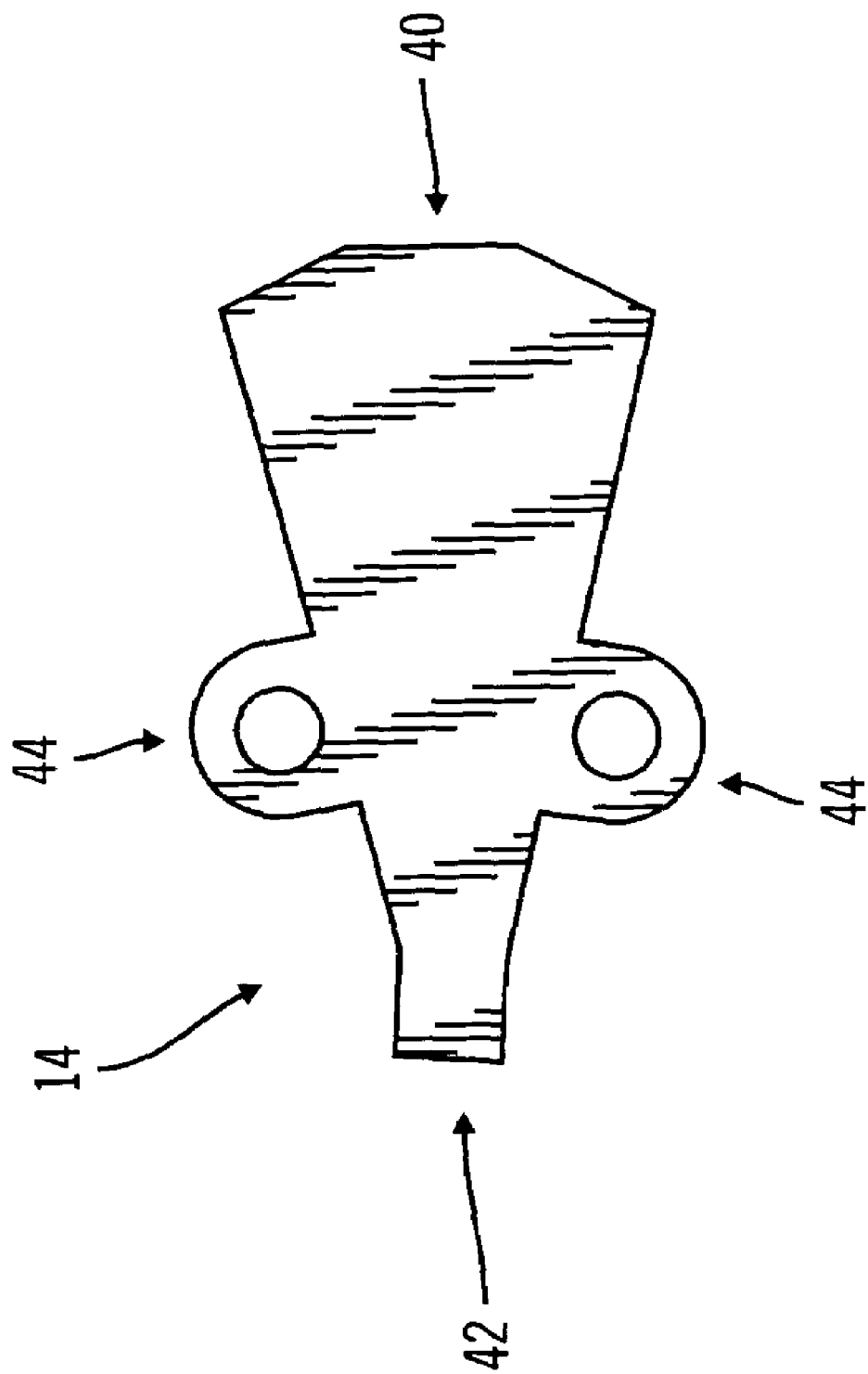
FIG. 3 shows a plan view of details of a junction element according to an embodiment of the present invention.

Details of a junction element 14 according to an embodiment of the present invention may be seen in FIG. 3. The junction element 14 in FIG. 3 comprises a first junction element end 40, a second junction element end 42 and suture tabs 44. In the embodiment shown in FIG. 3, the first junction element end 40 is arc-shaped and large enough so that it may accommodate various tubings and fittings. The second junction element end 42 is much narrower than the first junction element end 40 and is formed large enough so that it can accommodate the two infusion line tubings and the sensor tubing used in the shown embodiment. However, both the first junction element end 40 and the second junction element end 42 may be formed into a variety of shapes and sizes, dictated by the nature of the environment in which the catheter is used.

The suture tabs 44 may be used by a medical care provider to suture the junction element 14 onto the patient or to attach to some other surface. In this way, the risk that the catheter moves while in use is minimized. In addition to or alternative to the suture tabs 44, other means may be employed to fix the junction element 14 to the patient or other surface. For example, the junction element 14 may be formed with another type of tab or any other element that would facilitate immobilizing the catheter to the patient. For examples the suture tabs 44 could be adhesive rather than mechanical sewing. In addition, other shapes would also suffice as long as the risk of the suture shearing thorough the tags is minimized.

The junction element 14 may be made from a variety of materials. For example, according to one embodiment of the present invention, the junction element 14 is formed from liquid silicone rubber. However, a variety of plastics and other materials may be used. In addition, the junction element 14 is not limited to the shape shown in FIG. 3. The junction element 14 may be formed into any shape that facilitates its application.

Figure 4:
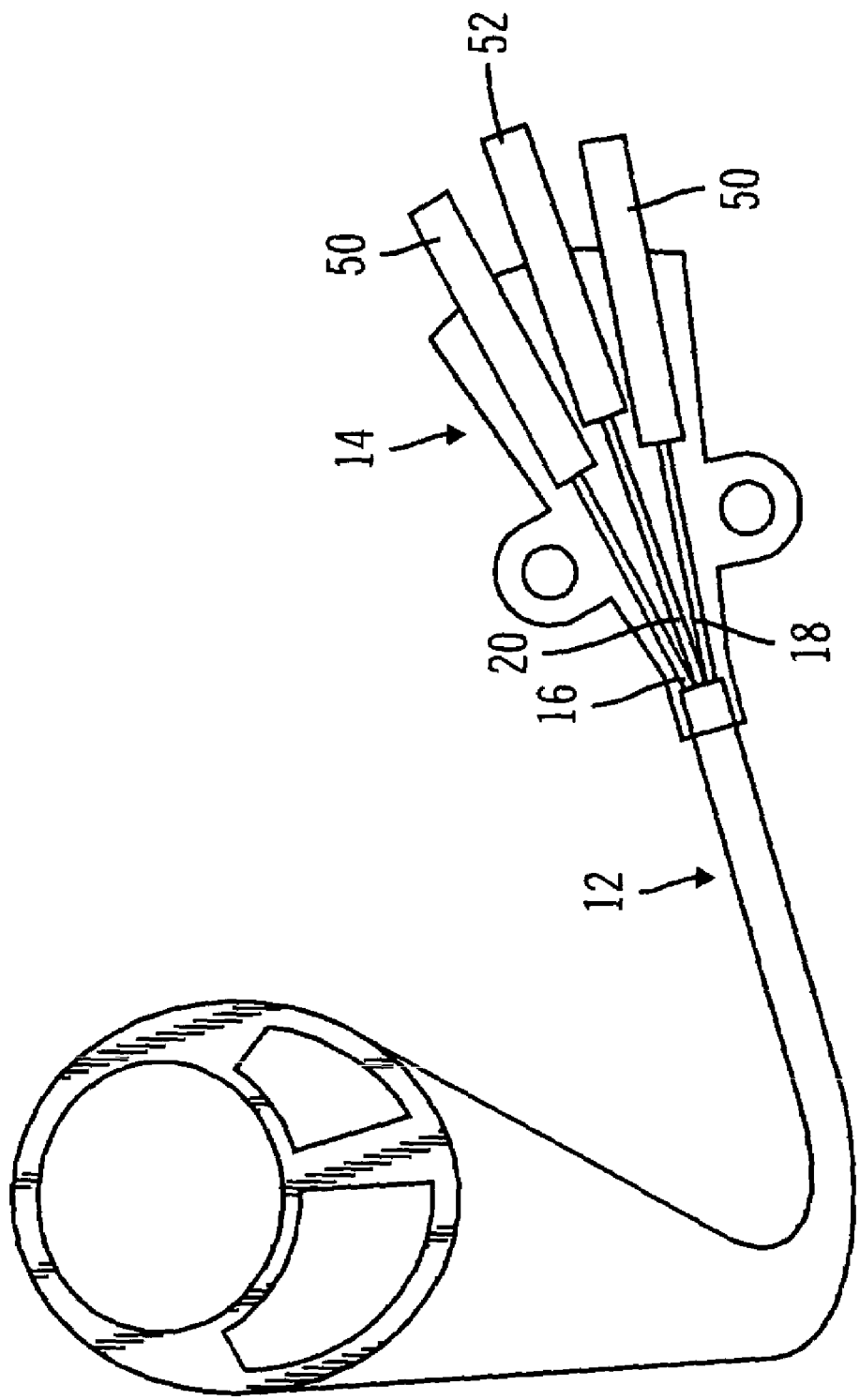
FIG. 4 shows a plan view of details of the union between the junction element and the lumen tubing according to an embodiment of the present invention.

FIG. 4 shows details of the union between the junction element 14 and the lumen tubing 12. The junction element 14 may be affixed to the lumen tubing 12 by a variety of methods. For example, according to an embodiment of the present invention, the lumen tubing 12 may be joined to the junction element 14 by a compression fit. According to another embodiment of the present invention, the junction element 14 may be bonded to the lumen tubing 12 using an adhesive. Suitable adhesives may include, but are not limited to, medical grade silicone adhesives or other medical grade adhesives. Depending on the materials used to fabricate the junction element 14 and the lumen tubing 12, a primer may be needed to facilitate an adhesive bond between the junction element 14 and the lumen tubing 12. Suitable primers may include, but are not limited to, adhesives diluted with heptane or other solvents.

Positioned within the junction element 14 are the first infusion tubing 16, the second infusion tubing 18 and the sensor line 20. The first infusion tubing 16, the second infusion tubing 18 and the sensor line 20 extend from their associated lumens within the lumen tubing 12 to the expanded portion of the junction element 14. According to one embodiment of the present invention, the tubings may adhesively attach to their associated lumens. According to another embodiment of the present invention, the tubings may be molded into place. At the expanded end of the junction element 14, the first infusion tubing 16 and the second infusion tubing 18 are fitted with infusion tubing core pins 50 while the sensor tubing 20 is fitted with a sensor tubing core pin 52. The infusion tubing core pins 50 and the sensor tubing core pin 52 maintain the shape and position of the first infusion tubing 16, the second infusion tubing 18 and the sensor tubing 20 as they extend through the junction element 14 into their associated lumens within the interior of the lumen tubing 12. In addition, the infusion tubing core pins 50 and the sensor tubing core pin 52 provide a larger surface with which to attach infusion lines and a sensor lead, respectively. The infusion tubing core pins 50 and the sensor tubing core pin 52 may be made from a variety of materials, including, but not limited to, stainless steel, titanium, delrin, TEFLON, or any metal or non-porous plastic. Whatever the material used, it should have a high melt point for hot transfers or a low melt point for cold molds.

Figure 5:
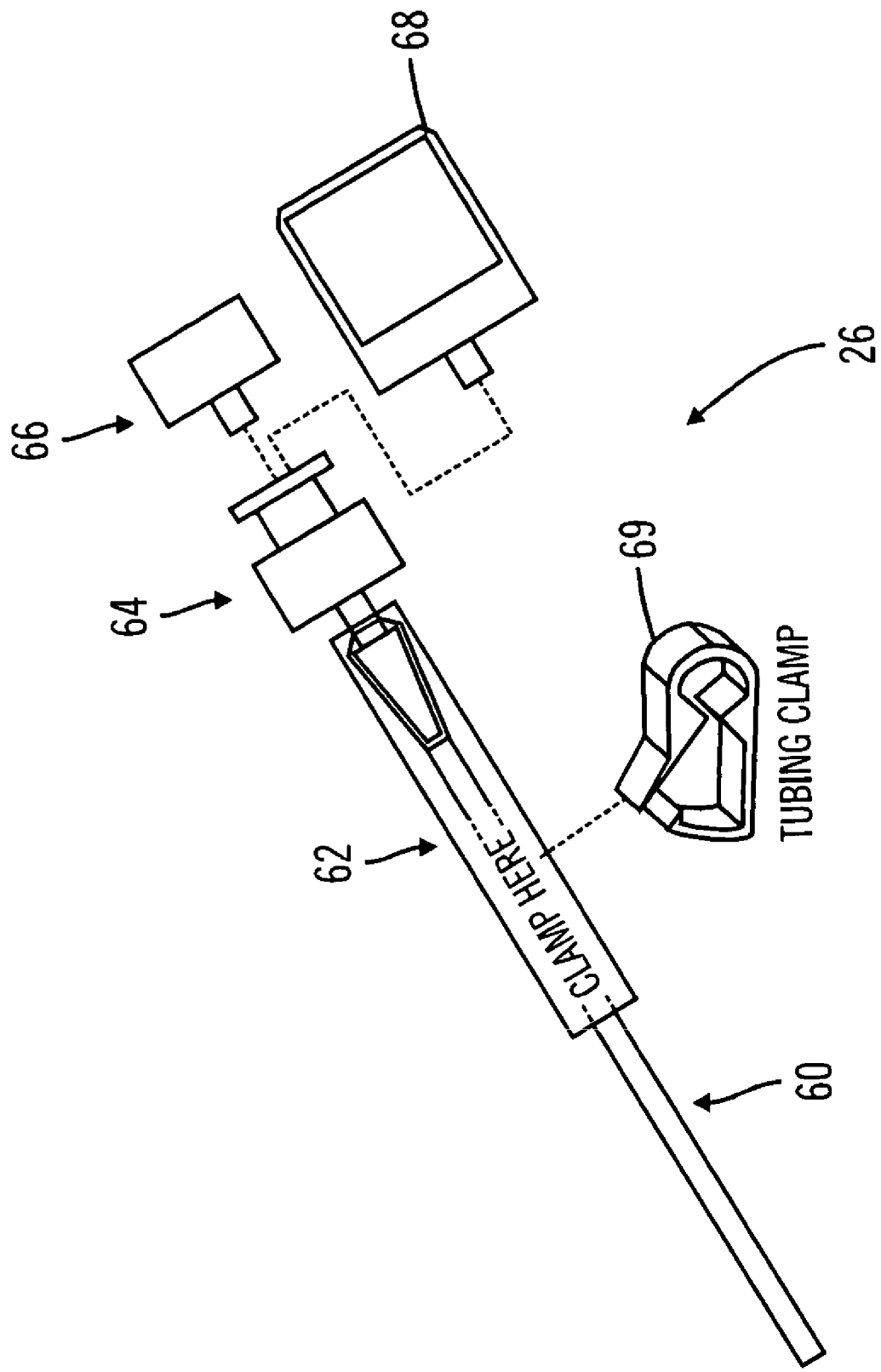
FIG. 5 shows a perspective view of an infusion member according to an embodiment of the present invention.

An infusion member 26 according to an embodiment of the present invention is shown in FIG. 5. The example infusion member 26 includes an infusion member lead tubing 60, a strain relief tubing 62, a female Luer fitting 64, a male Luer cap 66, and a male Luer injunction site 68. A tubing clamp 69 may also be used in connection with the infusion member 26. Any suitable tubing clamp structure may be used, including but not limited to, a spring action clamp 69 as shown in FIG. 5, a pinch clamp, slide clamp, roller clamp or the like.

The infusion member lead tubing 60 may comprise a silicone tubing and is generally inserted into a core pin. The strain relief tubing 62 provides support for the junction between the infusion member lead tubing 60 and the female Luer fitting 64 by stretching over the top of the infusion member lead tubing 60 and securing itself and the infusion member lead tubing 60 to the Luer fitting 64. Any materials suitable for the catheter would also be suitable for the strain relief tubing 62. Should it become necessary to restrict the flow of infusant travelling through the infusion member 2, the tubing clamp 69 may be positioned onto a deformable location of the infusion member 26, or the strain relief tubing 62, to clamp off the infusion member 26 and restrict the flow of infusant through the infusion member 26. The strain relief tubing 62 also holds the tubing clamp 69 so that the inner (and thinner) infusion member lead tubing 60 will not permanently deform if the clamp is secured for a long time. Moreover, by holding the tubing clamp 69, the infusion member lead tubing 60 may be less susceptible to fatigue stresses (e.g., from opening and closing the tubing clamp 69 repeatedly, movement of the infusion tubes or pulling on the infusion tubes during IV infusion) and accidental dislodgment of the tube from the fitting.

The male Luer cap 66 may be inserted into the female Luer fitting 64 when the infusion member 26 is not in use. When it becomes necessary to inject an infusant into the patient, the male Luer injection site 68 may be used in place of the male Luer caps 66. Although Luer fittings are used in the embodiment shown in FIG. 5, any type of fitting, such as a locking fitting, for example, that is appropriate for the application may be used in combination with the infusion member 26. Also, the male Luer caps 66 may have latex or non-latex septum or injection sites that may be used to receive needles or an IV drip system. Also, the male and female fittings may be reversed from the arrangement shown in FIG. 5.

The infusion members 26 and all associated caps, fittings, locks and the like may be color coded for easy identification. For example, an infusion member 26 used for blood may be color coded red while an infusion member 26 used for drugs, glucose or other medicants may be color coded white.

Figure 6:
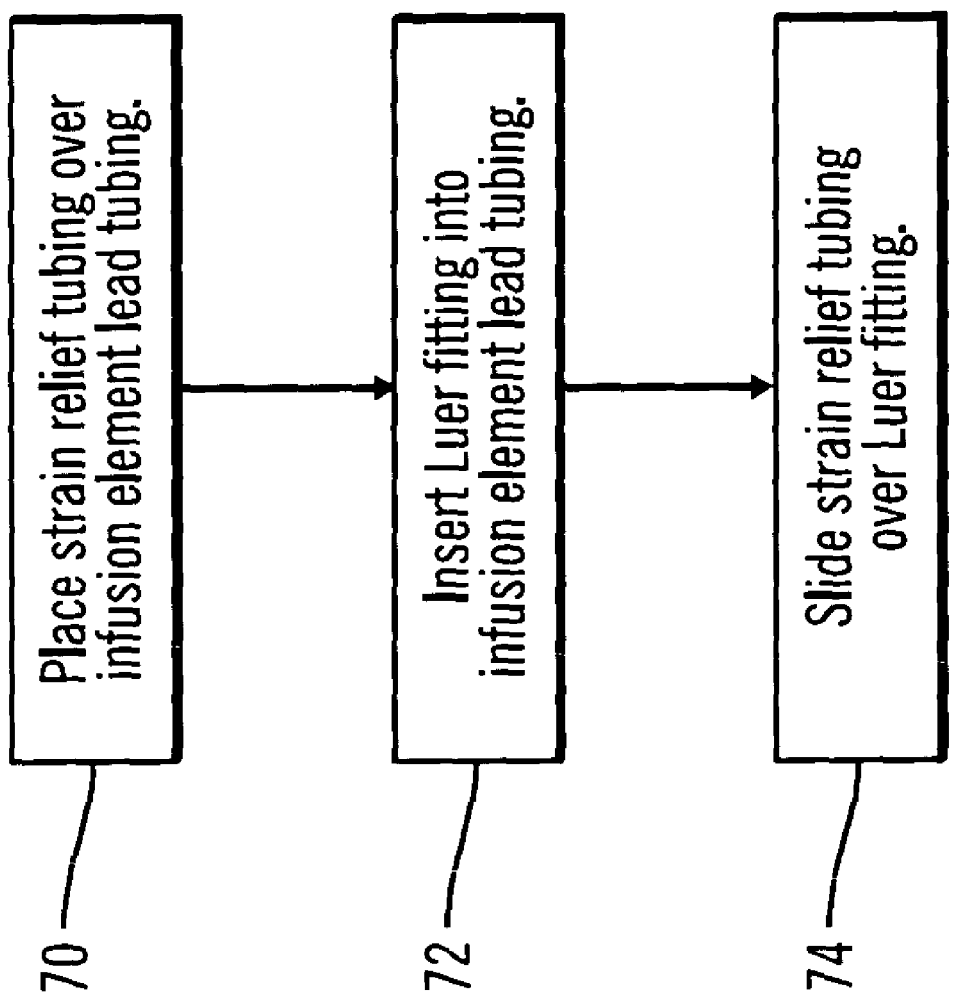
FIG. 6 shows a method for assembling an infusion member according to an embodiment of the present invention.

A method for assembling the infusion member 26 according to an embodiment of the present invention is shown in FIG. 6. At step 70, the strain relief tubing 62 is placed over the infusion member lead tubing 60. To facilitate this step, the hollow portion of the strain relief tubing 62 should be large enough to accommodate the diameter of the infusion member lead tubing 60, but not so large that it is ineffective to provide the desired strain relief. At step 72, the female Luer fitting 64 is inserted into the infusion member lead tubing 60. The position of the female Luer fitting 64 may be maintained by compression and the friction between the female Luer fitting 64 and the infusion member lead tubing 60.

Once the female Luer fitting 64 has been inserted into the infusion member lead tubing 60, the strain relief tubing 62 is then slid back toward the female Luer fitting 64 at step 74 so that it completely covers that portion of the female Luer fitting 64 that has been inserted into the infusion member lead tubing 60. Using the method shown in FIG. 6, the infusion member 26 may be assembled quickly and without adhesives. However, in other embodiments, adhesives may be used assemble the infusion member 26. In yet other embodiments, the catheter could be completely molded, i.e., plastic fittings could molded into the infusion line/junction/distal tube mold, or the fittings could be molded into the full part mold.

Figure 7:
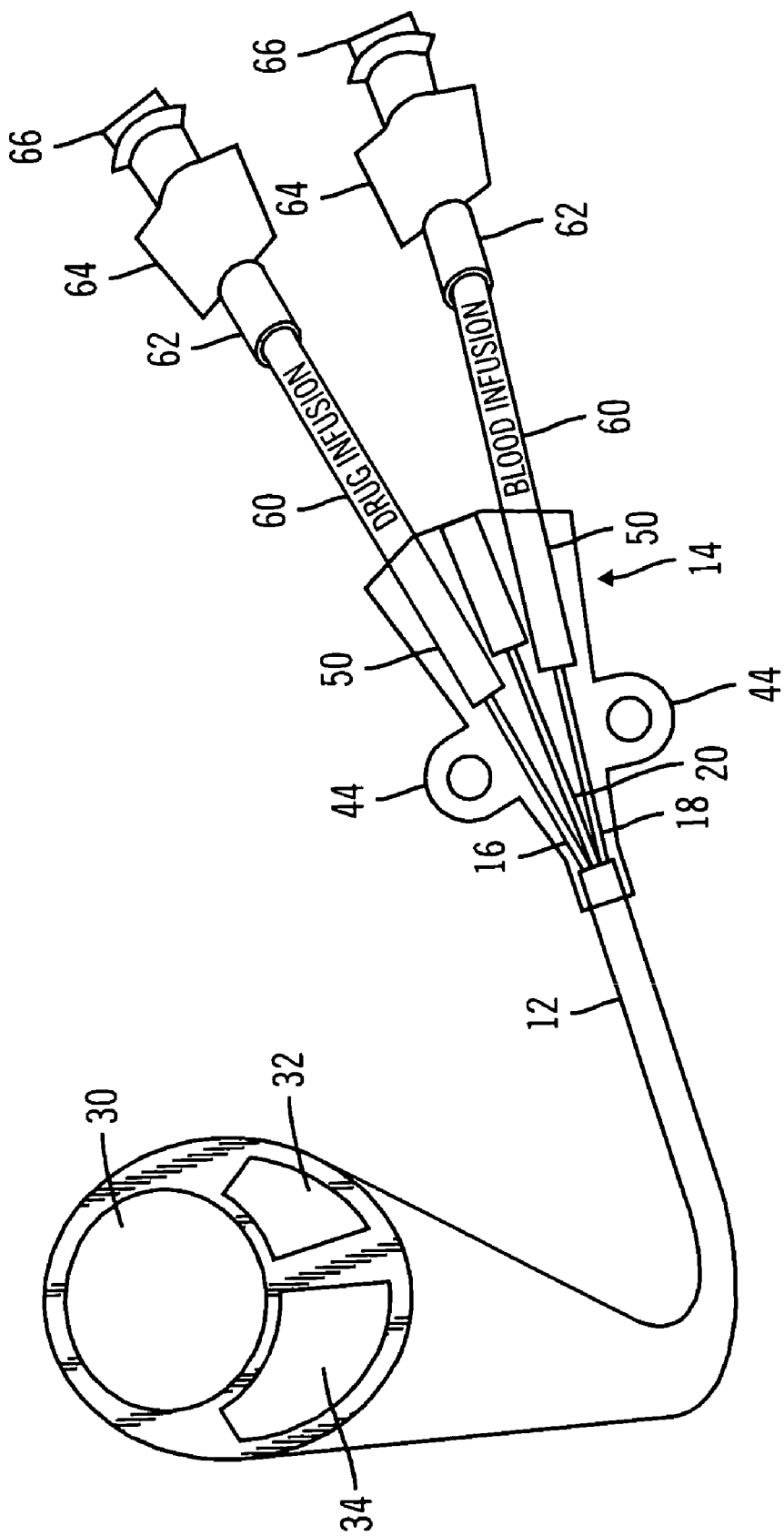
FIG. 7 shows a multilumen catheter assembly according to an embodiment of the present invention.

An assembled multilumen catheter assembly according to an embodiment of the present invention is shown in FIG. 7. Male Luer caps 66 have been inserted into female Luer fittings 64, which in turn have been inserted into infusion member lead tubings 60. Strain relief tubings 62 cover the junction between the female Luer fitting 64 and the infusion member lead tubing 60. The infusion member lead tubings 60 have been inserted into infusion tubing core pins 50 residing within the junction element 14. The infusion tubing core pins 50 may be affixed to the first infusion tubing 16 and the second infusion tubing 18. The sensor tubing core pin 52, also residing within the junction element 14, is affixed to the sensor tubing 20. The first infusion tubing 16, the second infusion tubing 18 and the sensor line 20 extend through the junction element 14 into the first infusion lumen 32, the second infusion lumen 34 and the sensor lumen 30, respectively. Within the junction element 14, the first infusion tubing 16, the second infusion tubing 18 and the sensor tubing 20 may be bonded in place with an adhesive or otherwise maintained in their relative positions.

The junction element 14 may be bonded to or otherwise affixed to the lumen tubing 12. For example, according to an embodiment of the present invention, the lumen tubing 12 may be molded into the junction element 14 with an angle on the core pins that stretch the lumen tubing 12 open within the mold to create a mechanical interference fit that cannot be easily pulled apart. The junction element 14 is also configured with suture tabs 44. Thus, the embodiment of the present invention shown in FIG. 7, once it has been equipped with a sensor lead having a sensing element, is ready for use. The lumen tubing 12 may be inserted into a patient, the suture tabs may be sutured to the patient and the Luer fittings may be affixed to drug and blood infusion lines for delivery of infusant to the patient. When the sensor lead 22 is connected to its associated electronics, the delivery of infusant to the patient may be automatically monitored and controlled.

FIG. 8a shows how a sensor lead 20 may be marked according to an embodiment of the present invention. A sensor scale 82 may be provided on the sensor as shown in FIG. 8a. Although the sensor scale 82 would typically be marked in elements of length such as centimeters, for example, the sensor scale 82 may be marked with any units desired for a particular application. The sensor scale 82 may be marked with ink or other permanent marking. Thus, if the lumen tubing 12 is made from a transparent or partially transparent material such as silicone, for example, the sensor scale 82 that has been inked onto the sensor line 20 may be seen directly through the lumen tubing 12. According to another embodiment of the present invention, an opaque tube with marking on the outside or makings that have been molded into an opaque part with later inking for greater definition may also be used.

Infusion members 26 may also be identified as shown in FIG. 8b according to an embodiment of the present invention. For example, infusion member lead tubings may be identified with lead tubing identifications 84. In the embodiment shown in FIG. 8, the lead tubing identifications 84 designate the actual gauge of the associated lumen, in this case, for example, 18-gauge. Also, the strain relief tubings 64 may be identified with clamping site identifications 86. Clamping site identifications 86 provide a visual indication for the site at which the tubing clamp 69 may be manually located.

Figure 9:
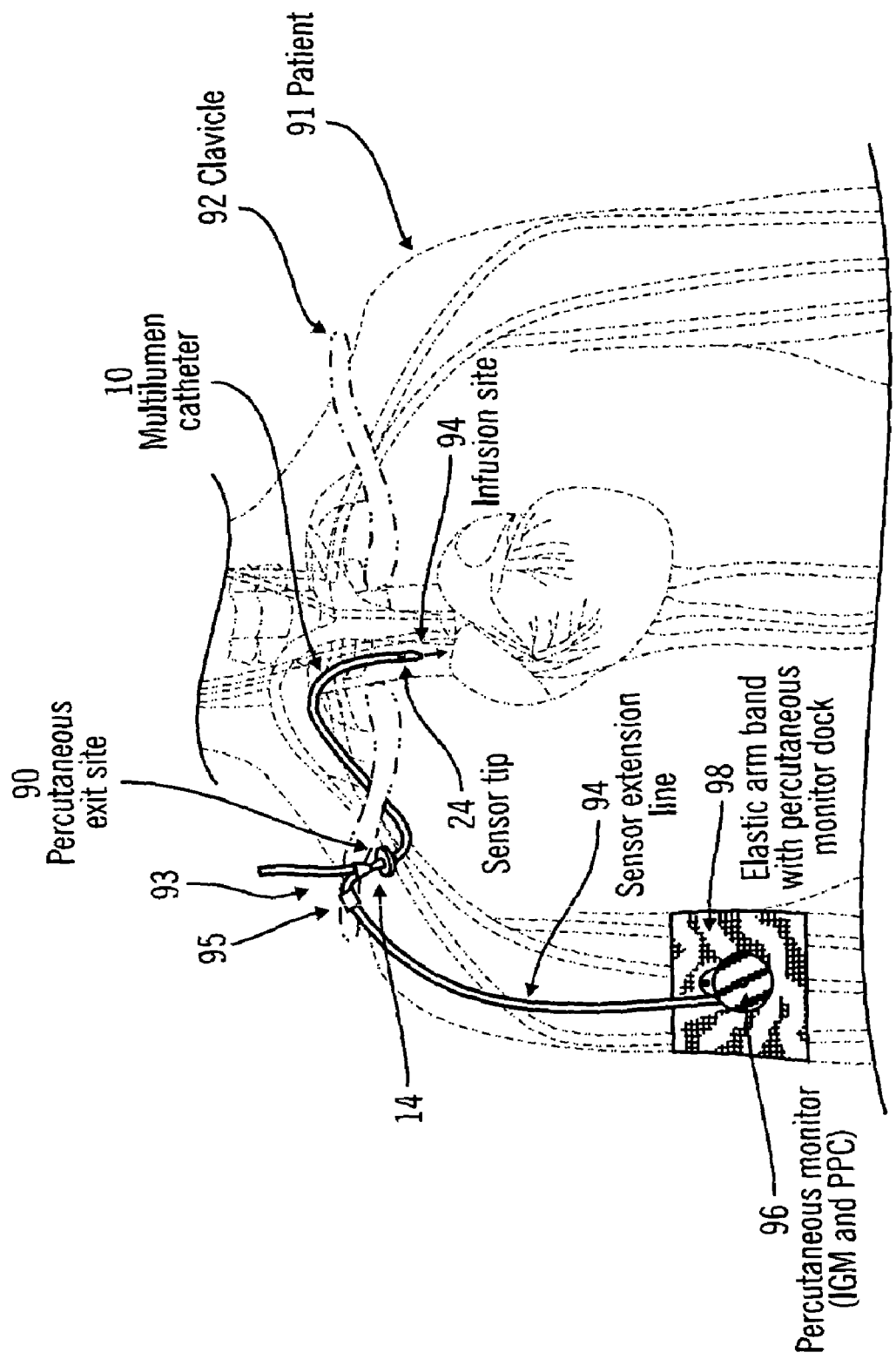
FIG. 9 shows a multilumen catheter implanted into a patient according to an embodiment of the present invention.

FIG. 9 shows the multilumen catheter 10 as it exists implanted into a patient according to an embodiment of the present invention. Insertion of the multilumen catheter 10 into the body may be accomplished via a subclavian vein, an internal jugular vein or other suitable manners. In the embodiment shown in FIG. 9, the entrance is through a subclavian vein. Thus, the multilumen catheter 10 is inserted at a percutaneous site 90 and routed underneath a clavicle 92. The multilumen catheter 10 is extended through the subclavian vein until the sensor tip 24 resides at a position desired by the physician, which will be dictated in part by the size and body characteristics of the patient 91. The junction element 14 rests in the general vicinity of the shoulder of the patient 91. Luer fitted infusion ports 93 and a sensor extension line connector 95 are external to the patient and may be connected to infusion lines and sensor electronics 94, respectively. The sensor extension line 94 may be connected to a percutaneous monitor 96, such as, for example, an in vivo glucose monitor or a personal pump communicator. The percutaneous monitor 96 may be affixed to the patient, such as, for example, by using an elastic armband 98.

According to the embodiment shown in FIG. 9, if a diabetic patient, for example, is in an intensive care or other critical care or medical care situation, the patient may be fitted with the multilumen catheter 10 for automatic monitoring of control and delivery of one or more infusants to the patient. For example, the multilumen catheter 10 may be inserted percutaneously into the patient through a subclavian vein. The sensor lead 22 may be directed to a desired location in the body, such as, the right atrial junction. In this manner, the sensing element 24 may rest at a location suitable for parameter monitoring, such as, glucose monitoring. The sensing element 24 may extend several inches past the end of the lumen tubing 12 or may extend to the end of the lumen tubing 12. Thus, even though the sensor lead 22 may be positioned in vivo, a medical care provider may determine how far into the body the sensor lead has extended by observing the markings on the sensor lead 22 that are external to the body in the vicinity of the junction element 14.

The junction element 14, which is external to the patient, may be sutured to the patient in the general vicinity of the shoulder area using the suture tabs 44. Infusant delivery systems may be connected to the infusion members 26 while the external portion of the sensor lead 22 may be connected to electronics. Once powered by the electronics, the sensing element 24 can sense glucose or other parameters, which are read by the electronics. The electronics in turn may control the infusant delivery systems to deliver infusants, such as, for example, blood, glucose, other medicants and the like to the infusion members 26. The infusant will travel through the infusion members 26 to the infusion lumens 32, 34 and exit the catheter at the end of the lumen tubing 12 where the lumens 32, 34 terminate, thus delivering the required treatment to the patient.

Embodiments of the present invention may be used percutaneously or may be implanted. For example, the multilumen catheter 10 may be used percutaneously or may be fully implanted.

Figure 10:
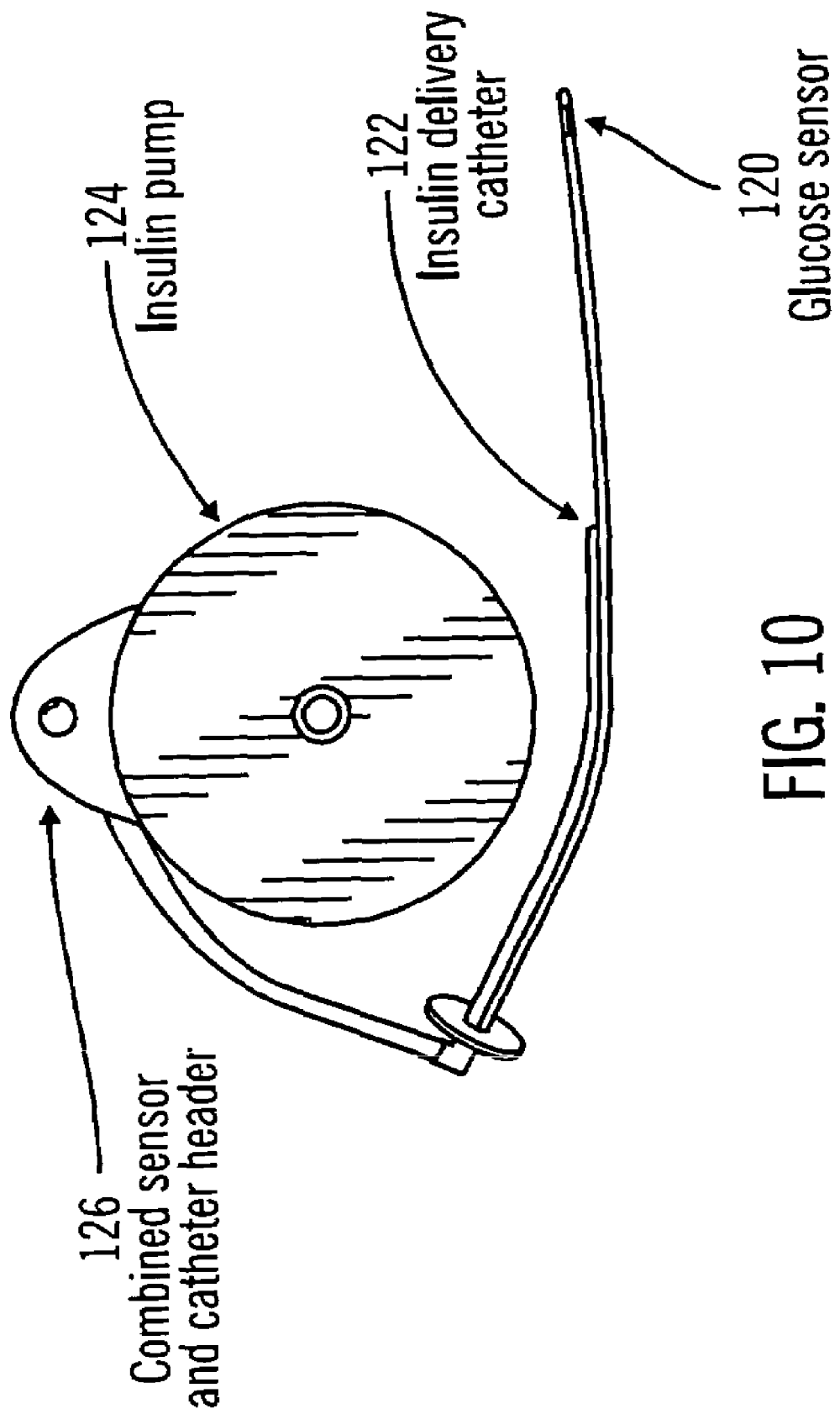

A combined insulin delivery catheter and sensor for peritoneal applications according to an embodiment of the present invention is shown in FIG. 10. The embodiment of the invention sown in FIG. 10 includes, without limitation, a sensor 120, which may be a glucose sensor, a delivery catheter 122, which may be an insulin delivery catheter, a pump 124, which may be an insulin pump, and a combined sensor and catheter header 126.

In the embodiment of the invention shown in FIG. 10, the glucose sensor 120 and the insulin delivery catheter 122 may be used percutaneously or may be implanted. If the insulin pump 124 and the sensor and catheter header 126 are designed to be implanted, the entire embodiment of the invention shown in FIG. 10 may be implanted into a patient. If the insulin pump 124 and the sensor and catheter header 126 are not designed to be implanted, the combined insulin delivery catheter 122 and glucose sensor 120 may be inserted percutaneously into the body and may extend out of the body and attach to the sensor and catheter header 126 and the insulin pump 124. Also, the embodiment of the invention shown in FIG. 10 may be used for peritoneal applications.

Embodiments of the present invention may also be directed to a single lumen catheter. For example, embodiments of the present invention may include a single lumen device having no other lumens that is used as a percutaneous device. The single lumen may be used for a sensor or for an infusant. For example, according to an embodiment of the present invention, a single lumen catheter may include a sensor used as a percutaneous device. Thus, a sensor may be inserted into the body and still extend outside of the body for connection to monitoring or control electronics or other devices. The sensor may be included in a sleeve or may be inserted with a sleeve that is later removed. The sensor may remain in the body for a period of time.

In a single lumen catheter according to embodiments of the present invention, the single lumen catheter may include elements described above in connection with a multilumen catheter. For example, the single lumen catheter may include a lumen tubing having a lumen within its interior, a junction element, a sensor tubing connected to the lumen within the interior of the lumen tubing, and a sensor lead. A distal end of the sensor lead may also include a sensing element. The single lumen catheter may also include Luer fittings and Luer caps.

Figure 11:
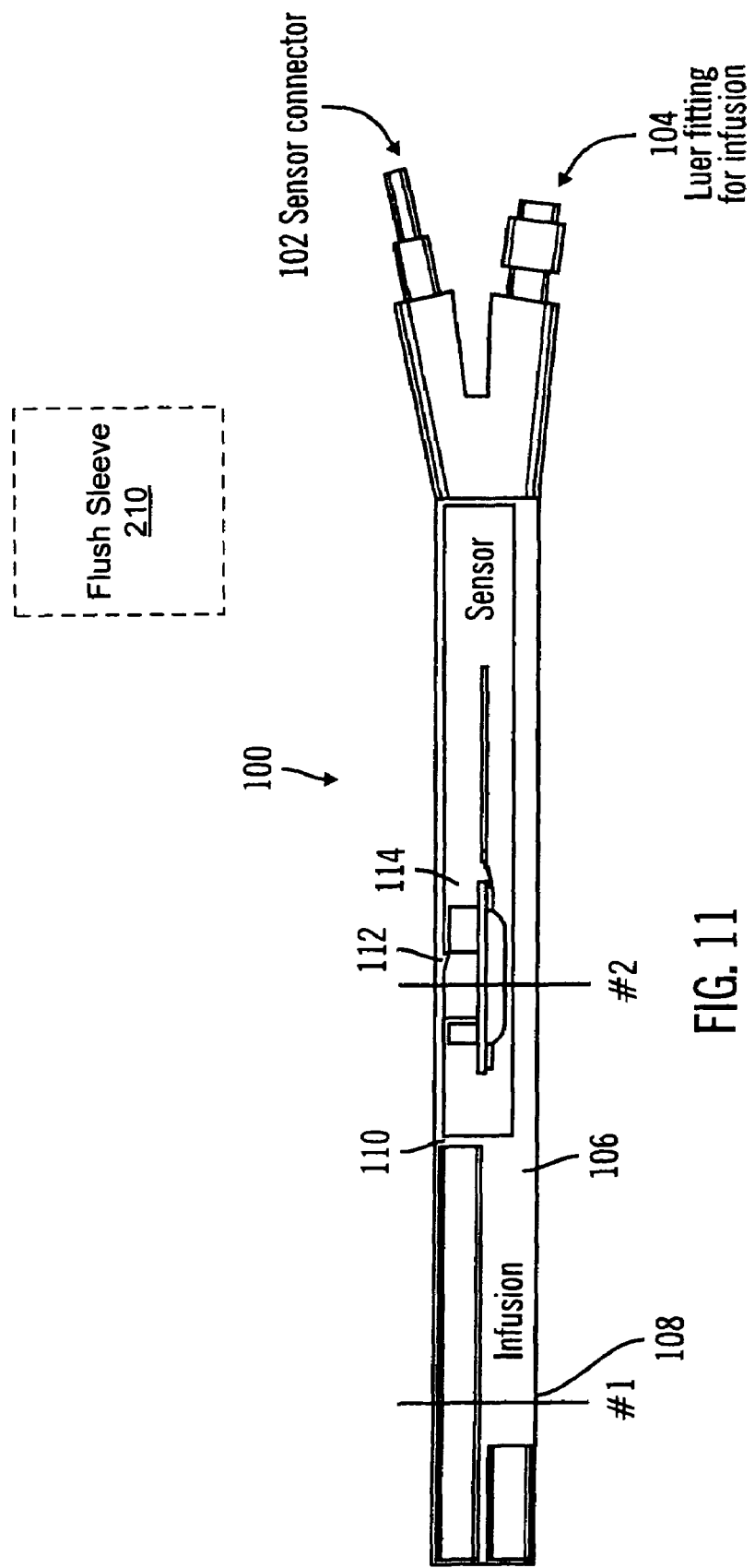
FIG. 11 is a schematic diagram illustrating a central line with an analyte sensor in accordance with the embodiments of the present invention.

Embodiments of the present invention may be directed to an improved central line catheter with a built in analyte and/or therapy sensor that determines body characteristics on a continuous, intermittent or near continuous basis. In addition to an improved central line catheter, embodiments of the invention may also be directed to an improved Swan-Ganz catheter or PICC line. FIG. 11 is a schematic diagram illustrating the central line catheter 100 with an analyte sensor 114 in accordance with the preferred embodiments of the present invention. Central line catheters are known in the art and typically used in the Intensive Care Unit (ICU)/Emergency Room of a hospital to deliver medications through one or more lumens of the catheter to the patient (different lumens for different medications). The central line catheter 100 is typically connected to an infusion device (e.g. infusion pump, IV drip, or syringe port) on one end and the other end inserted in one of the main arteries or veins near the patient's heart to deliver the medications. The infusion device (not shown) delivers medications, such as, but not limited to, saline, drugs, vitamins, medication, proteins, peptides, insulin, neural transmitters, or the like, as needed to the patient. In alternative embodiments, the central line catheter can be used in any body space or vessel such as intraperitoneal areas, lymph glands, the subcutaneous, the lungs, the digestive tract, or the like and may determine the analyte or therapy in body fluids other than blood.

The central line catheter 100 of FIG. 11 is shown as a double lumen catheter. In preferred embodiments of the present invention, the analyte sensor 114 is built into one lumen 110 of the central line catheter 100 and is used for determining characteristic levels in the blood and/or bodily fluids of the user. In the preferred embodiment, the analyte sensor 114 is a glucose sensor as generally described in U.S. Pat. Nos. 4,650,547; 4,671,288; 4,781,798; 4,703,756; and 4,890,620, which are incorporated by reference herein. However, it will be recognized that further embodiments of the invention may be used to determine the levels of other agents, characteristics or compositions, such as hormones, cholesterol, medications, concentrations, viral loads (e.g., HIV), or the like. Therefore, although embodiments of the present invention are primarily described in the context of glucose sensors used in the treatment of diabetes/diabetic symptoms, the embodiments of the invention are applicable to a wide variety of patient treatment programs where a physiological characteristic is monitored in an ICU.

As shown in FIG. 11, the sensor 114 is located in a first lumen 110 of the central line catheter 100. An orifice 112 exists in the first lumen 110 to allow blood to contact the sensor 114, and for the sensor 114 to collect data. The sensor 114 then sends the information through the sensor connector 102 to a monitor system (not shown), where the data can be processed and displayed. The monitor system presents the blood characteristic in real-time or near real-time format to allow for immediate monitoring of the patient's condition. The glucose sensor 114 generally includes, in one preferred form, an improved implantable enzyme electrode of the general type described in U.S. Pat. Nos. 4,650,547; 4,671,288; 4,781,798; 4,703,756; and 4,890,620, and more recently described in U.S. patent application Ser. No. 10/038,276, filed on Dec. 31, 2001, entitled "Sensor Substrate and Method of Fabricating the Same," U.S. patent application Ser. No. 10/036,093, filed on Dec. 28, 2001, entitled "Sensing Apparatus and Process," and U.S. patent application Ser. No. 10/034,338, filed on Dec. 28, 2001, entitled "Implantable Sensor Electrodes and Electronic Circuitry" which are incorporated by reference herein. Such enzyme electrodes include a sensor tip for direct contact with patient fluids, such as blood. The sensor tip defines a conductivity sensor for measuring fluid conductivity changes in response to an enzymatic reaction typically involving the use of glucose oxidase to catalyze glucose in the presence of oxygen ($O_2$). Conductivity signals are transmitted through the sensor 114 via conductors to a proximal end of the sensor 104 to the monitor system via the sensor connector 102.

In alternative embodiments, different sensor technology may be used, such as, but not limited to an optical sensor. Preferably, and implantable optical sensor would include a photo-reactive substance or compound that optically changes, fluoresces, or the like, or other suitable compounds that detect changing properties in the presence of a bodily fluid analyte, such as glucose or the like. The compounds can also be used to detect the level of an analyte that has been ingested, injected or placed inside the body, such as marker substances, or the like. For example, possible compounds, including but not limited to, produce a fluorescent change in the presence of a bodily fluid analyte are disclosed in U.S. Pat. No. 5,503,770 issued Apr. 2, 1996 to James et al. and entitled "Fluorescent Compound Suitable For Use In The Detection Of Saccharides"; U.S. Pat. No. 5,512,246 issued Apr. 30, 1996 to Russell et al. and entitled "Method and Means for Detecting Polyhydroxyl Compounds"; U.S. Provisional Application Ser. No. 60/007,515 to Van Antwerp et al. and entitled "Minimally Invasive Chemically Amplified Optical Glucose Sensor"; and U.S. Pat. No. 6,011,984 to Van Antwerp et al. and entitled "Detection of Biological Molecules Using Chemical Amplification", all of which are herein incorporated by reference. Other compounds using Donor Acceptor fluorescent techniques maybe used, such as disclosed in U.S. Pat. No. 5,628,310 issued May 13, 1997 to Rao et al. and entitled "Method and Apparatus to Perform Trans-cutaneous Analyte Monitoring"; U.S. Pat. No. 5,342,789 issued Aug. 30, 1994 to Chick et al. and entitled "Method and Device for Detecting and Quantifying Glucose in body Fluids"; and U.S. Pat. No. 5,246,867 issued Sept. 21, 1993 to Lakowicz et al. and entitled "Determination and Quantification of Saccharides by Luminescent Lifetimes and Energy Transfer", all of which are herein incorporated by reference.

In the preferred embodiments where the sensor is a glucose sensor and characteristic to be determined is a blood glucose level, the glucose monitor is generally of the type described in U.S. patent application Ser. No. 09/511,580, filed on Feb. 23, 2000, entitled "Glucose Monitor Calibration Methods", which is herein incorporated by reference. In alternative embodiments, the glucose monitor is generally of the type described in U.S. patent application Ser. No. 09/377,472, filed Aug. 19, 1999, entitled "Telemetered Characteristic Monitor System And Method Of Using The Same", which is incorporated by reference herein.

In preferred embodiments, the monitor system contains both a monitor, which attaches to the sensor 114 and records the raw sensor data; and a data processor (not shown), which contains the software and programming instructions to download and evaluate data recorded by the monitor. However, in alternative embodiments, the monitoring process electronics can be built into separate devices. In addition, although the monitor system takes raw sensor data from the sensor 114 and assesses it during real-time in preferred embodiments, the monitor system can also store the raw data for later processing or downloading to the data processor. In alternative embodiments, the monitoring system may include a display that is used to display the calculated results of the raw glucose sensor data received via a download from the glucose monitor. The results and information displayed includes, but is not limited to, trending information of the characteristic (e.g., rate of change of glucose), graphs of historical data, average characteristic levels (e.g., glucose), stabilization and calibration information, raw data, tables (showing raw data correlated with the date, time, sample number, corresponding blood glucose level, alarm messages, and more), and the like.

In alternative embodiments, the monitor system may also be combined with other medical devices to accept other patient data through a common data network and/or telemetry system. For example, a glucose monitor may be combined with a blood glucose meter to directly import or correlate glucose calibration reference values such as described in U.S. patent application Ser. No. 09/334,996, filed Jun. 17, 1999, entitled "Characteristic Monitor With A Characteristic Meter and Method Of Using The Same", which is incorporated by reference herein. The glucose monitor may also be combined with semi-automated medication infusion pumps of the external type, as generally described in U.S. Pat. Nos. 4,562,751; 4,678,408; and 4,685,903; or automated implantable medication infusion pumps, as generally described in U.S. Pat. No. 4,573,994, which are herein incorporated by reference, or hospital based IV infusion systems. The glucose monitor may record data from the infusion pumps and/or may process data from both the glucose sensor 114 and an infusion pump to establish a closed loop system to control the infusion pump based on glucose sensor measurements. In other embodiments, other body characteristics are monitored, and the monitor may be used to provide feedback in a closed loop system to control a drug delivery rate.

As shown in FIG. 11, a second lumen 106 is provided in the central line catheter 100 for the purpose of delivering medication directly to a main artery or vein near the heart. In preferred embodiments an orifice 108 is used to release medication into the bloodstream, and a Luer fitting 104 is used to connect with an infusion pump, IV drip, or syringe port. However, in alternative embodiments, more than one orifice 108 can be formed in the second lumen 106 to deliver medication into the bloodstream. In addition, the connection fitting between the second lumen 106 and the infusion device can be a plug-in connector is similar to a jack/plug combination, a septum cap, or other similar device instead of Luer fitting.

Figure 12:
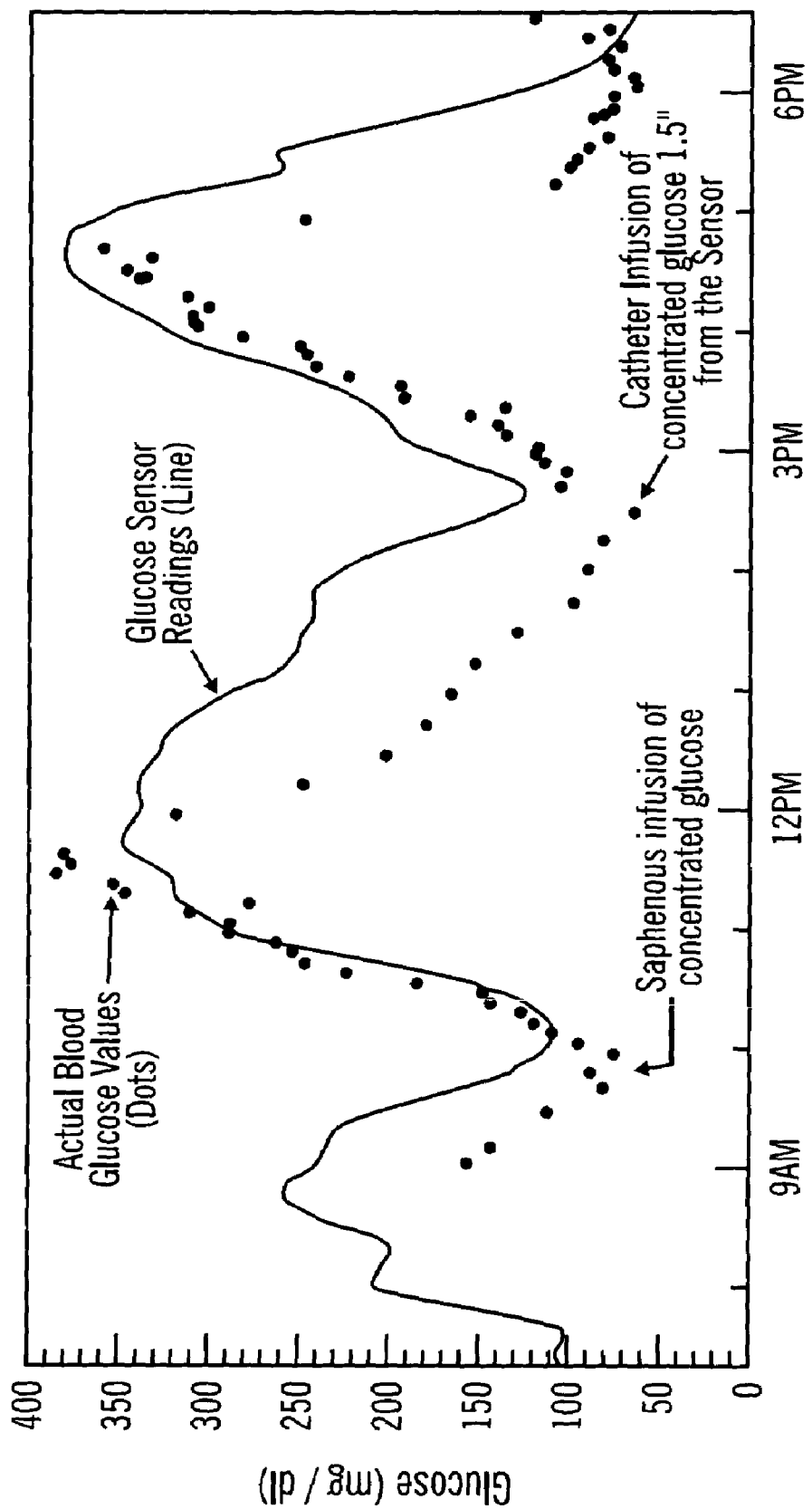
FIG. 12 is a graph of a study performed using the central line with an analyte sensor in accordance with the embodiments of the present invention.
Figure 14:
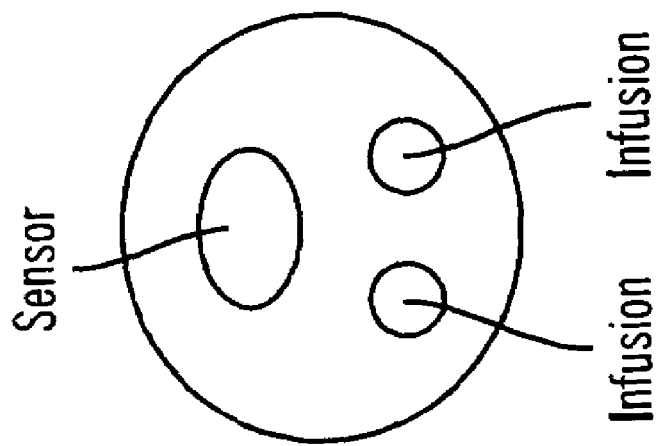
FIG. 14 illustrates another alternative embodiment of the central line catheter in accordance with the embodiments of the present invention.

In preferred embodiments, the orifice 108 of the second lumen 106 is located a set distance closer to the proximal end of the central line 100 than the sensor orifice 112 of the first lumen 110. By ensuring that the orifice 108 is further downstream of the blood flow compared to the sensor orifice 112, the sensor 114 is ensured that any readings taken by the sensor 114 will not be corrupted or distorted by the delivery of any form of medication from the orifice 108. FIG. 12 describes a study performed using the central line 100 with an analyte sensor 114 to prove that no interference occurs between the drug infusion (or any other type of infusion) and the sensor reading. The study of FIG. 12 used a glucose sensor 114 to detect if there were any differences in response when administering a dextrose solution (i.e., a concentrated glucose solution) through a peripheral location (i.e., saphenous infusion) versus administering through the central line catheter 100. The study showed that there was no interference between the delivery of dextrose solution and the sensor 114 using the central line catheter 100 of the present invention. An interference would have been detected if a spike in the glucose readings occurred when the dextrose was administered through the central line catheter 100.

Figure 13:
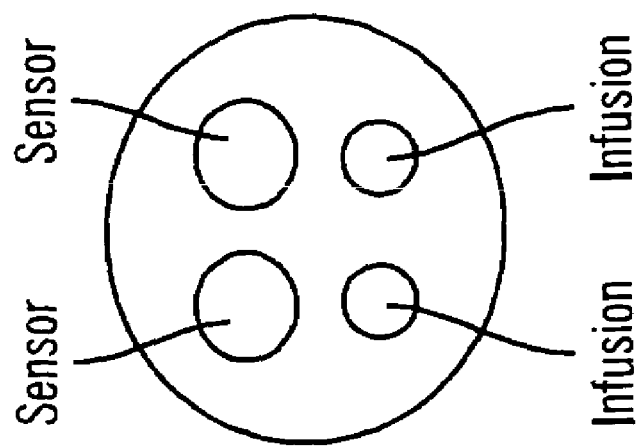
FIG. 13 illustrates an alternative embodiment of the central line catheter in accordance with the embodiments of the present invention.

Although in the preferred embodiments, a double lumen central line catheter was shown, any additional number of lumens could be added to the central line catheter 110. FIGS. 12 and 13 illustrate alternative embodiments of the central line catheter in accordance with the preferred embodiments of the present invention. As shown in FIGS. 12 and 13, multiple infusion lumens and multiple sensors can be placed in the central line catheter. The additional lumens can be used to deliver other type of fluids, such as, but not limited to, saline, vitamins, drugs, medication, proteins, peptides, insulin, neural transmitters, or the like, as needed to the patient. Additional sensors can be added to detect different characteristics from the body of the patient. In addition, in alternative embodiments, additional lumens can be used to perform other functions. For example, additional smaller lumens can be located within the first lumen 110 or second lumen 106 of FIG. 11 to deliver saline or other suitable cleansing fluid to clean the orifices 108 or 112 in case clotting agents, proteins, fats, or other substances in the blood tend to cover the orifices 108 and 112. Alternatively, a flush sleeve 210 can be placed around the entire central line catheter 100, as described in U.S. patent application Ser. No. 10/034,740, filed Dec. 27, 2001, entitled "Implantable Sensor Flush Sleeve," which is incorporated by reference herein. The flush sleeve 210 will have orifices directed where the sensor would take readings and/or where the central line catheter would deliver the medications.

Figure 15:
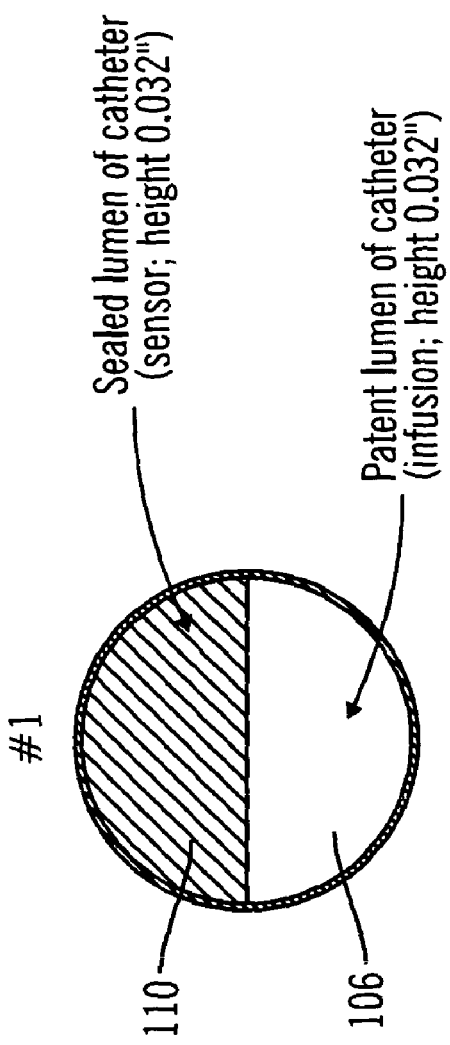
FIG. 15 is a cross-sectional view of the central line along line #1 of FIG. 10, in accordance with the embodiments of the present invention.

FIG. 15 is a cross-sectional view of the central line along line #1 of FIG. 11, in accordance with the preferred embodiments of the present invention. FIG. 15 illustrates how the unsealed portion of the second lumen 106 extends past the location of the sensor in the first lumen 110, ensuring that the sensor orifice 112 is located downstream of the infusion orifice 108.

Figure 16:
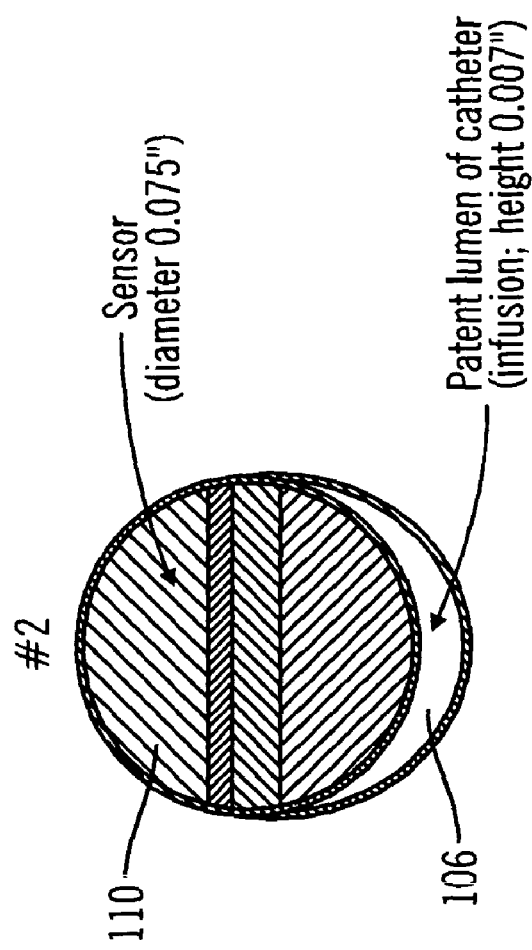
-FIG. 16 is a cross-sectional view of the central line along line #2 of FIG. 10, in accordance with the embodiments of the present invention.

FIG. 16 is a cross-sectional view of the central line along line #2 of FIG. 11, in accordance with the preferred embodiments of the present invention. FIG. 16 illustrates how the central line catheter 100 can be modified to include the sensor 114 without increasing the typical size of a double lumen catheter. By reducing the size of the second lumen 106 along the portion of the length of the first lumen 110 containing the sensor 114, the sensor 114 can be easily accommodated in the central line catheter 100.

Thus, the analyte sensor can be combined within a central line catheter to measure an analyte level in vivo in the body of a patient, while administering other fluids through the central line catheter.

Although the preferred embodiments described the ability use a central line catheter to administer medications while collecting characteristic data through a sensor, other modifications are possible to the device to perform other functions. The central line catheter can also be used to sample directly from the patient's body. Thus, the ability to sense, sample, and infuse provides a wide range of diagnostic and therapeutic options. In addition, various combinations of the features can be used. For example, the central line catheter can sense what is being infused, infuse an agent which positively or negatively impacts what is being sensed, or sensing, infusing and sampling can be unrelated.

While particular embodiments of the present invention have been shown and described, it will be obvious to those skilled in the art that the invention is not limited to the particular embodiments shown and described and that changes and modifications may be made without departing from the spirit and scope of the appended claims.

What is claimed is:

1. A multilumen catheter comprising:
    a first tubing;
    a plurality of lumens disposed within the first tubing, each lumen of the plurality of lumens having a first end and a second end, said plurality of lumens include a sensor lumen;
    a plurality of second tubings;
    a junction element maintaining a connection between the first end of each lumen of the plurality of lumens and a corresponding second tubing of the plurality of second tubings; and
    a sensor lead having a sensing element that extends through the sensor lumen;
    wherein the sensor lumen has a shape and size that provides a compression fit for the sensor lead; and
    wherein the sensing element is able to exit the first tubing at an end of the first tubing and is able to extend past the end of the first tubing and is able to extend past the second end of each lumen of the plurality of lumens.

2. The multilumen catheter of claim 1, further comprising infusion members for attachment to the plurality of second tubings.

3. The multilumen catheter of claim 1, wherein the plurality of lumens are extruded from the first tubing.

4. The multilumen catheter of claim 1, further comprising a lubricious coating on the first tubing.

5. The multilumen catheter of claim 4, wherein the lubricious coating is siloxane.

6. The multilumen catheter of claim 1, wherein the plurality of second tubings comprise a first infusant tubing, a second infusant tubing and a sensor tubing.

7. The multilumen catheter of claim 6, wherein the plurality of lumens further include a first infusant lumen and a second infusant lumen.

8. The multilumen catheter of claim 7, wherein the first infusant tubing is connected to the first infusant lumen, the second infusant tubing is connected to the second infusant lumen and the sensor tubing is connected to the sensor lumen.

9. The multilumen catheter of claim 7, wherein the first infusant lumen and the second infusant lumen exit the first tubing at the same distance along the length of the first tubing.

10. The multilumen catheter of claim 7, wherein the first infusant lumen and the second infusant lumen exit the first tubing at different distances along the length of the first tubing.

11. The multilumen catheter of claim 8, wherein the sensing element is able to extend up to several inches past the second end of each lumen of the plurality of lumens.

12. The multilumen catheter of claim 11, wherein the sensing element is a glucose analyte sensor.

13. The multilumen catheter of claim 11, wherein the sensing element is an analyte sensor.

14. The multilumen catheter of claim 8, further comprising infusion members connected to the first infusant tubing and the second infusant tubing.

15. The multilumen catheter of claim 14, wherein the infusion members comprise injection sites.

16. The multilumen catheter of claim 1, wherein the sensing element is able to extend up to several inches past the second end of each lumen of the plurality of lumens.

17. The multilumen catheter of claim 16, wherein the sensing element is able to extend up to several inches past the end of the first tubing.

18. The multilumen catheter of claim 16, wherein the sensor lead is positioned proximal to the first tubing.

19. The multilumen catheter of claim 1 further comprising:
a generally circular catheter body;
wherein the sensor lumen is inside the catheter body and has a generally oval shape; and
wherein the second tubing is inside the catheter body and has a cross sectional shape that has one edge facing the sensor lumen and a curvature corresponding to that of the generally oval shaped sensor lumen, and the second tubing has a second edge facing the catheter body and a curvature corresponding to that of the generally circular shaped catheter body.

20. The multilumen catheter of claim 1, wherein the multilumen catheter is a Swan-Ganz catheter.

21. The multilumen catheter of claim 1, wherein the multilumen catheter is a Peripherally Inserted Central Catheter.

22. The multilumen catheter of claim 1,
wherein the sensing element is able to extend past the end of the first tubing and is able to extend past the second end of each lumen of the plurality of lumens such that the sensing element is not in contact with the first tubing and is not in contact with any of the plurality of lumens.

23. The multilumen catheter of claim 1, wherein the sensor lumen has a generally oval cross-sectional shape.

24. The multilumen catheter of claim 23, wherein the plurality of lumens includes a plurality of lumens arranged around the sensor lumen, each of said plurality of lumens arranged around the sensor lumen having a cross-sectional shape that curves at least partially around the generally oval cross-sectional shape of the sensor lumen.

25. A system in an intensive care unit, the system comprising:
a central line catheter, the central line catheter comprising:
a sensor lead having a sensing element capable of indicating a characteristic level in blood;
a first lumen for delivering fluid to a body of a patient, the first lumen having an exit site at which the fluid is able to exit into the body of the patient; and
a second lumen for containing at least a portion of the sensor lead, the second lumen having an end that is adapted to be located in the body of the patient when the first lumen is delivering the fluid to the body of the patient;
an infusion device for delivering the fluid through the first lumen; and
a monitoring device for displaying readings obtained by the sensor;
wherein the sensor is able to extend past the exit site of the first lumen and is able to extend past the end of the second lumen; and
wherein the second lumen has a generally oval shape that provides a compression fit for the sensor lead.

26. The system of claim 25,
wherein the sensor is able to extend past the end of the second lumen such that the sensor is not in contact with the second lumen.

27. The system according to claim 25, further comprising:
a generally circular catheter body;
wherein the second lumen is inside the catheter body and has a generally oval shape; and
wherein the first lumen is inside the catheter body and has a cross sectional shape that has one edge facing the second lumen and a curvature corresponding to that of the generally oval shaped second lumen, and the first lumen has a second edge facing the catheter body and a curvature corresponding to that of the generally circular shaped catheter body.

* * * * *